US011226322B2

United States Patent
Heffels et al.

(10) Patent No.: US 11,226,322 B2
(45) Date of Patent: *Jan. 18, 2022

(54) OPTICAL GAS ANALYZER AND METHOD FOR MEASURING NITROGEN OXIDES IN AN EXHAUST GAS

(71) Applicant: Siemens Aktiengesellschaft, Munich (DE)

(72) Inventors: Camiel Heffels, Stutensee-Büchig (DE); Daniel Roßfeld, Glan-Münchweiler (DE)

(73) Assignee: Siemens Aktiengesellschaft, Munich (DE)

( * ) Notice: Subject to any disclaimer, the term of this patent is extended or adjusted under 35 U.S.C. 154(b) by 374 days.

This patent is subject to a terminal disclaimer.

(21) Appl. No.: 16/383,034

(22) Filed: Apr. 12, 2019

(65) Prior Publication Data

US 2019/0317067 A1  Oct. 17, 2019

(30) Foreign Application Priority Data

Apr. 13, 2018 (EP) .................... 18167338

(51) Int. Cl.
*G01N 31/00* (2006.01)
*G01N 21/33* (2006.01)
(Continued)

(52) U.S. Cl.
CPC ......... *G01N 33/0037* (2013.01); *F01N 11/00* (2013.01); *G01N 21/3151* (2013.01); *G01N 31/005* (2013.01)

(58) Field of Classification Search
CPC ............... G01N 31/00; G01N 33/0013; G01N 33/0009; G01N 21/3151; G01N 33/0037; G01N 21/33; B01D 53/30; B01D 53/56
(Continued)

(56) References Cited

U.S. PATENT DOCUMENTS 3,652,227 A * 3/1972 Harman, III ......... G01N 31/002
436/118
3,718,429 A * 2/1973 Williamson ........... G01N 21/75
436/118
(Continued)

FOREIGN PATENT DOCUMENTS

CN     101663573     3/2010
CN     102449464     5/2012
(Continued)

OTHER PUBLICATIONS

Higashi Ryoichi et al.: "A NOx and SO2 gas analyzer using deep-UV and violet light-emitting diodes for continuous emissions monitoring systems", Proc. SPIE 9003, Light-Emitting Diodes: Materials, Devices, and Applications for Solid State Lighting XVIII, 90031F, pp. 1-6; 2014.
(Continued)

*Primary Examiner* — Arlen Soderquist
(74) *Attorney, Agent, or Firm* — Cozen O'Connor (57) ABSTRACT

Gas analyzer and method for measuring nitrogen oxides in an exhaust gas, wherein to measure the nitrogen oxides, ozone is generated from oxygen, the exhaust gas is treated with the ozone generated to convert nitrogen monoxide within the exhaust gas into nitrogen dioxide, the nitrogen dioxide concentration in the treated exhaust gas is measured photometrically using a first light-emitting diode which emits with a central wavelength between 350 nm and 500 nm and output as the nitrogen oxide concentration in the exhaust gas, and the ozone concentration in the treated exhaust gas is measured photometrically using a second light-emitting diode which emits with a central wavelength between 250 nm and 265 nm, where generation of the ozone using the measured ozone concentration as an actual value is regulated to a prespecified setpoint value to enable reliable
(Continued)

continuous measurement of nitrogen oxides in exhaust gases with a low outlay on equipment.

17 Claims, 5 Drawing Sheets

(51) Int. Cl.
*G01N 33/00* (2006.01)
*F01N 11/00* (2006.01)
*G01N 21/31* (2006.01)

(58) Field of Classification Search
USPC .............. 422/82.09, 91; 436/116, 118, 171
See application file for complete search history.

(56) References Cited

U.S. PATENT DOCUMENTS

| | | | |
|---|---|---|---|
| 3,835,322 A * | 9/1974 | Komatsu | G01N 31/005 436/118 |
| 4,078,896 A * | 3/1978 | Moen | G01N 21/534 356/418 |
| 4,314,344 A * | 2/1982 | Johns | G01N 33/0006 204/176 |
| 5,614,723 A | 3/1997 | Oppenlander et al. | |
| 5,739,038 A * | 4/1998 | Burrows | G01N 21/31 422/199 |
| 6,493,087 B1* | 12/2002 | Fabinski | G01N 21/3504 235/439 |
| 6,791,689 B1* | 9/2004 | Weckstrom | G01J 3/10 356/437 |
| 10,871,443 B2* | 12/2020 | Heffels | G01N 21/33 |
| 2010/0028819 A1 | 2/2010 | Knittel et al. | |
| 2010/0061885 A1 | 3/2010 | Harley | |
| 2011/0062056 A1 | 3/2011 | Tate et al. | |
| 2011/0177607 A1 | 7/2011 | Akasaka et al. | |
| 2012/0070334 A1 | 3/2012 | Ehrhorn et al. | |
| 2012/0170043 A1* | 7/2012 | Rao | G01N 21/39 356/437 |
| 2015/0153272 A1 | 6/2015 | Ehring et al. | |
| 2020/0200674 A1* | 6/2020 | Heffels | G01N 33/0024 |
| 2021/0132019 A1* | 5/2021 | Heffels | F01N 11/00 |

FOREIGN PATENT DOCUMENTS

| | | | |
|---|---|---|---|
| CN | 105424631 | | 3/2016 |
| CN | 107158910 | | 9/2017 |
| CN | 206906240 U | | 1/2018 |
| CN | 107764774 | | 3/2018 |
| DE | 4314510 | * | 11/1994 |
| EP | 0697374 | | 2/1996 |
| EP | 2157421 | | 2/2010 |
| JP | 51-3289 | * | 1/1976 |
| JP | 52-119988 | * | 10/1977 |
| JP | S60119443 | | 6/1985 |
| JP | 62-221422 | * | 9/1987 |
| JP | 11-211663 | * | 8/1999 |
| JP | 2012026331 | | 2/2012 |
| JP | WO2015181879 | | 4/2017 |
| WO | 2015/181879 | * | 12/2015 |
| WO | WO2016112943 | | 7/2016 |

OTHER PUBLICATIONS

Office Action dated May 31, 2021 issued in Chinese Patent Application No. 201910297199.1.

* cited by examiner

OPTICAL GAS ANALYZER AND METHOD FOR MEASURING NITROGEN OXIDES IN AN EXHAUST GAS

BACKGROUND OF THE INVENTION

1. Field of the Invention

The invention relates to a gas analyzer for measuring nitrogen oxides in an exhaust gas with an oxidation device, which comprises an ozone generator for the generation of ozone from oxygen and is embodied to treat the exhaust gas with the ozone in order to convert nitrogen monoxide contained in the exhaust gas into nitrogen dioxide, a first light-emitting diode that emits with a central wavelength of between 350 nm and 500 nm, a second light-emitting diode that emits with a central wavelength of between 250 nm and 265 nm, a measuring chamber through which the treated exhaust gas flows and the light from the first light-emitting diode and the light from the second light-emitting diode passes, a detector that detects the light from the first light-emitting diode and the light from the second light-emitting diode after it has passed through the measuring chamber and which generates a detector signal with a first signal component resulting from the light from the first light-emitting diode and a second signal component resulting from the light from the second light-emitting diode and an evaluation device, which ascertains the nitrogen dioxide concentration in the treated exhaust gas in the measuring chamber from the first signal component and outputs this as the nitrogen oxide concentration in the exhaust gas and ascertains the ozone concentration in the exhaust gas in the measuring chamber from the second signal component.

The invention further relates to a method for measuring nitrogen oxides in an exhaust gas, where ozone is generated from oxygen, the exhaust gas is treated with the ozone generated to convert nitrogen monoxide contained in the exhaust gas into nitrogen dioxide, the nitrogen dioxide concentration in the treated exhaust gas is measured photometrically using a first light-emitting diode that emits with a central wavelength of between 350 nm and 500 nm and output as the nitrogen oxide concentration in the exhaust gas and the ozone concentration in the treated exhaust gas is measured photometrically using a second light-emitting diode that emits with a central wavelength of between 250 nm and 265 nm.

2. Description of the Related Art

WO 2015/181879 A1 discloses a conventional method and a gas analyzer.

The publication by Ryoichi Higashi et al.: "A NOx and SO2 gas analyzer using deep-UV and violet light-emitting diodes for continuous emissions monitoring systems", Proc. SPIE 9003, Light-Emitting Diodes: Materials, Devices, and Applications for Solid State Lighting XVIII, 90031F (Feb. 27, 2014), discloses a gas analyzer for measuring nitrogen oxides (NOx) and sulfur dioxide (SO2) in an exhaust gas. Before analysis, the exhaust gas is treated in two stages, where, in a first stage, nitrogen monoxide contained in the exhaust gas (NO) is converted with the aid of ozone (O3) into nitrogen dioxide (NO2) that can be measured by the gas analyzer. The ozone is generated from atmospheric oxygen via an electric discharge and fed to the exhaust gas. In a second treatment stage, the exhaust gas is heated to approximately 300° C. to induce thermal decomposition of excess ozone and dinitrogen pentoxide (N2O5) formed by the reaction of nitrogen dioxide and ozone and which cannot be measured by the gas analyzer into nitrogen dioxide. Hence, the concentration of nitrogen dioxide ascertained by the gas analyzer is a measure for the concentration of nitrogen oxides in the exhaust gas.

For the greatest possible conversion of nitrogen monoxide into nitrogen dioxide, the ozone must be generated with a certain excess. However, during the subsequent thermal decomposition of dinitrogen pentoxide, in addition to nitrogen dioxide, the formation of unwanted nitrogen monoxide is again possible and hence the heating of the exhaust gas should be controlled. Herein or as a result of disturbances, it is also possible that thermal decomposition of the excess ozone may be incomplete.

With the conventional gas analyzer, a light-emitting diode with an emission wavelength of 280 nm and a light-emitting diode with an emission wavelength of 400 nm are arranged close to one another in an LED array. A collimator lens shapes their light into a parallel light bundle, which passes through a measuring chamber, through which the treated exhaust gas flows, and is then focused on a detector. A beam splitter between the collimator lens and the measuring chamber diverts a part of the light to a monitor detector. The light-emitting diodes are switched on and off alternately to detect the sulfur dioxide contained in the exhaust gas at the absorption wavelength 280 nm and nitrogen dioxide at the absorption wavelength 400 nm. The detector signal is normalized with the signal of the monitor detector before being evaluated to ascertain the sulfur dioxide and nitrogen dioxide or nitrogen oxide concentrations in the exhaust gas. The temperature of the light-emitting diodes is regulated to a constant value by means of a Peltier element.

With the gas analyzer disclosed in the above-cited WO 2015/181879 A1, the ozone for treating the exhaust gas is generated from ambient air by silent electric discharge and mixed with the exhaust gas. The ozone generation or the ozone generator are switched on and off by the evaluation device of the gas analyzer. When the ozone generator is switched on, the nitrogen dioxide concentration in the treated exhaust gas is ascertained photometrically at a central wavelength of between 350 nm and 500 nm and the ozone concentration at a central wavelength of between 240 nm and 330 nm. When the ozone generator is switched off, the nitrogen dioxide concentration in the untreated exhaust gas is ascertained. The concentrations ascertained both when the ozone generator is switched on and switched off and a value for the generated ozone, which is either known or measured via an ozone meter in the ozone generator, are used to calculate the nitrogen monoxide concentration in the exhaust gas. The central wavelength of between 240 nm and 330 nm, in particular 280 nm, can be used to ascertain the sulfur dioxide concentration in the exhaust gas when the ozone generator is switched off.

WO 2016/112943 A1 also discloses an arrangement for the conversion of nitrogen monoxide via ozone, which cannot be measured directly with present-day means into measurable nitrogen dioxide. The ozone is generated in an ozone generator from ambient air with the aid of UV light, for example, a mercury vapor lamp with a wavelength of 184.9 nm and then mixed with the sample gas (here: sample air) in an oxidation unit for the oxidation of the constituent nitrogen monoxides. Here, once again the problem is encountered that, particularly with a high ozone generation rate, in addition to ozone, unwanted higher nitrogen oxides are generated, while, with a low ozone generation rate, the ozone concentration is too low, on the one hand, to effect rapid and complete conversion of nitrogen monoxide into nitrogen dioxide and, on the other, to keep dilution of the air to be measured to a minimum. For this reason, therefore, a silica gel filter is arranged downstream of the oxidation unit to filter out or absorb higher nitrogen oxides, such as nitrogen dioxide, nitrogen trioxide (NO3) and dinitrogen pentoxide.

EP 2 157 421 A1 discloses a method for assaying the sulfur content entailing the combustion of a sample of the fuel and the determination of the concentration of sulfur dioxide in the exhaust gas by an ultraviolet fluorescence method. To avoid impairment of the measurement by nitrogen monoxide, the exhaust gas is first exposed in a container to light (185 nm) from a low-pressure mercury discharge lamp to generate ozone from the residual oxygen content ozone and thus convert nitrogen monoxide into nitrogen dioxide.

EP 0 697 374 A1 discloses a through-flow excimer lamp for treating fluids (gas or liquids) with UV radiation. A typical excimer emitter comprises a cylindrical, double-walled quartz tube that is filled with a noble gas, such as xenon, in the ring space between the walls. Electrodes situated outside on the inner and outer wall of the quartz tube are connected to a radio-frequency generator (RF generator). As a result of the radio-frequency high voltage, electrodes induce micro-discharges in the discharge volume via which excimer molecules are formed. The excimer molecules decay shortly after their generation, where, in the case of xenon, in each case, a 172 nm UV photon is emitted. In the case of the through-flow excimer lamp, the inner tube acts as a through-flow section for the fluid to be treated. The inner electrode is formed as a wire coil, which is in contact with the fluid, while the outer electrode envelopes the double-walled quartz tube and functions as a reflector for the UV radiation. To achieve a high degree of efficiency with the UV treatment of liquids, the inner electrode can be formed as a static mixer for the fluid. As a result of the mixing action, demixing is prevented, so that, for example, air or oxygen bubbles can be transported with the water during the treatment of polluted water. Oxygen enrichment in the water can accelerate the breakdown of pollutants considerably. Ozone formation can also be achieved via the UV radiation.

US 2010/061885 A1 discloses a gas analyzer for measuring ozone in a gas mixture, such as air, with which a measuring chamber containing the gas mixture is irradiated with the light of a light-emitting diode with a central wavelength of between 250 nm and 290 nm, in particular 265 nm. The light is then detected and evaluated to ascertain the ozone concentration.

JP 2012 026331 A discloses treating the exhaust gas in a motor vehicle with ozone, where a nitrogen monoxide-nitrogen dioxide ratio of 1:1 is desired to optimize the nitrogen oxide reduction in a downstream SCR catalyst. To ensure that no excess ozone reaches the environment, a semiconductor sensor is arranged in the exhaust gas path immediately ahead of the vehicle's muffler and its signal used to regulate the ozone generation. The ozone is generated via high voltage from ambient air and mixed with the exhaust gas.

US 2015/153272 A1 discloses an absorption photometer with two or more UV LEDs for detecting the concentration of proteins, peptides, nucleic acid etc. in solutions.

JP S60 119443 A discloses a non-dispersive infrared (NDIR) two-beam gas analyzer with a sample cell, a parallel reference cell and an opto-pneumatic detector with two reception chambers adjacent to one another. For measurement of nitrogen monoxide in a sample gas (exhaust gas), the gas is first guided through the sample cell then, via an oxidation device, through the reference cell. In the oxidation device, oxygen contained in the exhaust gas is converted into ozone by silent electric discharge or by UV light with which the nitrogen monoxide is turn completely converted into nitrogen dioxide. The two reception chambers are filled with nitrogen monoxide and are therefore only selective with respect to this gas component so that the two-beam gas analyzer measures the nitrogen monoxide concentration in the sample gas without interference from further concomitant gases.

SUMMARY OF THE INVENTION

It is an object of the invention to provide a gas analyzer and method that enable a reliable, continuous measurement of nitrogen oxides in exhaust gases with low outlay on equipment.

This and other objects and advantages are achieved in accordance with the invention by a gas analyzer having a regulating device that controls the ozone generator, which obtains the ascertained ozone concentration as an actual value in order to regulate this to a prespecified setpoint value.

With respect to the method of the invention, the object is achieved by regulating the generation of the ozone using the measured ozone concentration as an actual value to a prespecified setpoint value.

The regulation of the ozone generator or of the generation of the ozone with the ozone concentration values measured in the treated exhaust gas ensures that only an amount of ozone sufficient for the conversion of nitrogen monoxide into nitrogen dioxide is produced. Since, as a result, little or no excess ozone is produced, the conversion of nitrogen monoxide into nitrogen dioxide is almost complete, thereby achieving linear measurement of the nitrogen monoxide with the inexpensive LED nitrogen dioxide gas analyzer.

The first and second light-emitting diodes can be arranged in a manner that is known per se close to one another in an LED array or their light can be combined via a beam splitter to form a light bundle through the measuring chamber. For referencing (normalizing) the measurements, the (or a) beam splitter is preferably configured to divert a part of the light from the two light-emitting diodes to a reference detector, which generates a reference signal with first and second reference-signal components resulting from the light from the first and second light-emitting diode. Referencing of the two signal components of the detector signal with the associated reference-signal components is then performed in the evaluation device, such as by quotient formation. To enable differentiation of the different signal components of the detector signal and the reference signal, the light-emitting diodes can be actuated in succession in time-division multiplexing mode or their light can be modulated differently on generation and, for example, demodulated phase-sensitively on detection.

The ozone generation in the oxidation device can occur in various ways. However, the ozone generation mentioned in the Ryoichi Higashi et al. publication from atmospheric oxygen by means of electric discharge (corona discharge) has the disadvantage of the formation of nitrogen oxide compounds that are undesirable for the measurement of the nitrogen oxide in the exhaust gas. Therefore, the oxidation device of the gas analyzer in accordance with the invention preferably comprises an ozone generator with at least one ultraviolet light source that generates high-energy radiation with a wavelength of less than 240 nm (wavelength components greater than 240 nm result in the destruction of the ozone formed). In principle, suitable ultraviolet light sources are low-pressure mercury discharge lamps or electrodeless excimer lamps. The ultraviolet light source preferably comprises at least one xenon excimer emitter characterized by long life, low temperature dependence, easy dimming and the total absence of mercury.

Lean combustion with excess air advantageously enables the ozone to be generated completely from the residual oxygen content of the exhaust gas. Here, the ultraviolet light source is arranged in a closed reaction chamber through which exhaust gas flows. The reaction chamber can be formed as a tube, for example, with an internal mirror coating (for example, an aluminum tube) in which the, for example, cylindrical, ultraviolet light source extends. To enhance performance during the conversion of nitrogen monoxide into nitrogen dioxide, a plurality of such tubes can be connected in parallel. Alternatively, it is possible to use at least one through-flow excimer lamp, such as that disclosed in the aforementioned EP 0 697 374 A1.

If the performance of the ultraviolet light source deteriorates over time, then the exhaust gas can be additionally supplied with atmospheric oxygen. It is also possible to generate the ozone from atmospheric oxygen and mix it with the exhaust gas to be treated.

Despite the current widespread use of low-sulfur fuels, in many cases there is also a requirement to measure sulfur dioxide during the analysis of exhaust gases. To this end, the gas analyzer in accordance with the invention can comprise a third light-emitting diode that emits with a central wavelength of between 250 nm and 300 nm, the light from which also passes through the measuring chamber and is then detected by the detector. Therefore, the detector signal contains a third signal component from which the evaluation device ascertains the sulfur dioxide concentration in the exhaust gas. Here, once again, the first and second light-emitting diodes or all three light-emitting diodes can be arranged close to one another in an LED array or their light can be combined via at least one beam splitter into a light bundle through the measuring chamber. Furthermore, here, once again, a part of the light from the three light-emitting diodes can be diverted to a reference detector for referencing the measurements.

The cross-sensitivity between the residual concentration of the ozone in the treated exhaust gas and the measurement of the sulfur dioxide concentration in the aforementioned wavelength range of 250 nm and 300 nm can be compensated with the measured residual ozone concentration by computational measures.

Alternatively, it is possible to measure the sulfur dioxide concentration in the untreated exhaust gas. In addition, it is also advantageously possible to measure the nitrogen dioxide concentration in the untreated exhaust gas so that the nitrogen monoxide concentration in the exhaust gas can be ascertained from the difference between the nitrogen dioxide concentrations ascertained in the treated exhaust gas and in the untreated exhaust gas.

If the ozone is not generated exclusively from the residual oxygen content of the exhaust gas, it is, for example, possible for the additional oxygen supplied (for example, atmospheric oxygen) first to be guided with the exhaust gas through the first measuring chamber and measured there before it arrives at the oxidation device.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

For further explanation of the invention, reference is made to the figures in the drawing, in which.

DETAILED DESCRIPTION OF THE EXEMPLARY EMBODIMENTS

Identical parts and parts with identical functions are given the same reference numbers in each case.

Figure 1:
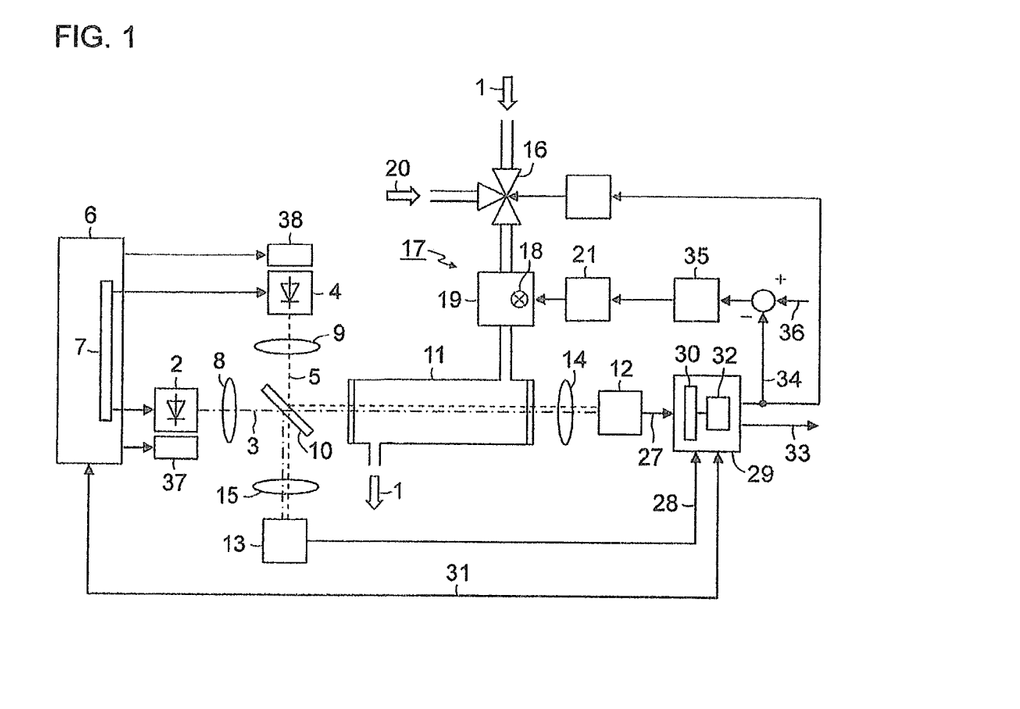
FIG. 1 is a first exemplary embodiment of the gas analyzer in accordance with the invention for measuring nitrogen oxides.

FIG. 1 is a simplified schematic representation of a block diagram of a gas analyzer for measuring nitrogen oxides in an exhaust gas 1. A first light-emitting diode 2 generates light 3 in the wavelength range of between 350 nm and 500 nm, for example, with a central wavelength of 405 nm. A second light-emitting diode 4 generates light 5 in the wavelength range of between 250 nm and 265 nm, for example, with a central wavelength of 254 nm. Both light-emitting diodes 2, 4 are actuated by a control device 6 which, in the exemplary embodiment depicted here, contains a multiplexer 7 in order to switch the light-emitting diodes 2, 4 on and off alternately. The light 3, 5 emitted by the light-emitting diodes 2, 4 is shaped via collimator lenses 8, 9 into parallel light bundles (hereinafter, called light beams) and supplied to a beam splitter 10, preferably a "polka-dot" beam splitter, with constant reflection/transmission over a wide spectral range. The beam splitter 10 splits the light 3, 5 from the light-emitting diodes 2, 4 into a partial beam through a measuring chamber 11 to a detector 12 and a further partial beam to a reference detector 13. The respective partial beams are focused via lenses 14, 15 on the detectors 12, 13, which in this case are photodiodes.

Following pretreatment (not shown here) comprising dehumidification via gas cooling, condensate separation and fine-particle filtration, the exhaust gas 1 is first guided via an optional controllable three-way mixing valve 16 through an oxidation device 17 before arriving in the measuring chamber 11. The exhaust gas flow can be adjusted to prespecified through-flow values and kept constant in a manner that is known per se by pressure regulation or flow regulation. After flowing through the measuring chamber 11, the exhaust gas 1 is discharged therefrom.

The oxidation device 17 comprises an ozone generator 18 in the form of an ultraviolet light source in a closed reaction chamber 19 through which the exhaust gas 1 flows. With its UV radiation at wavelengths of less than 240 nm, the ultraviolet light source 18 generates ozone from the residual oxygen in the exhaust gas 1 and the nitrogen monoxide contained in the exhaust gas 1 reacts with this ozone in the reaction chamber 19 to form nitrogen dioxide and some higher nitrogen oxides, mainly nitrogen trioxide and dinitrogen pentoxide. However, the higher nitrogen oxides only form when too much ozone is produced in the ozone generator 18. On the other hand, if only little or no excess ozone is produced, almost complete conversion of nitrogen monoxide into nitrogen dioxide occurs.

The controllable three-way mixing valve 16 is used to mix atmospheric oxygen 20 with the exhaust gas 1 when the residual oxygen content of the exhaust gas 1 or the performance of the ozone generator 18 are not sufficient to generate the amount of ozone required for the complete conversion of nitrogen monoxide into nitrogen dioxide. The ultraviolet light source 18 can be dimmed and is supplied or actuated by an operating device 21.

Figure 2:
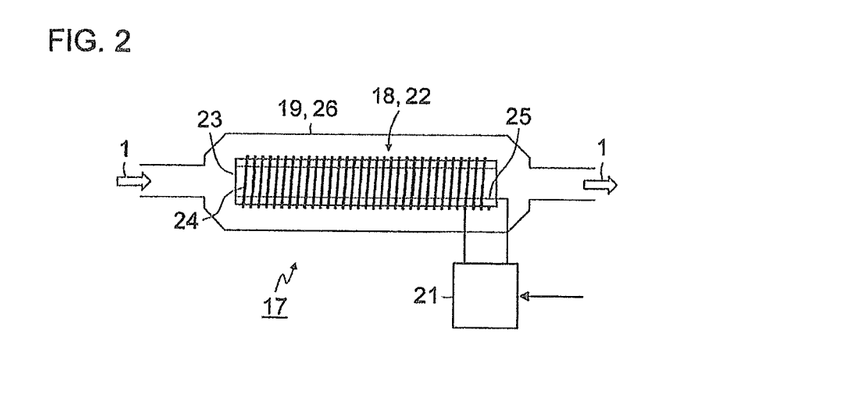
FIG. 2 is an exemplary embodiment of the ozone generator in accordance with the invention.

FIG. 2 is a very simplified illustration of an exemplary embodiment of the oxidation device 17, here, with an ultraviolet light source 18 in the form of a commercially available xenon excimer emitter 22. This comprises, in a known manner, a cylindrical, double-walled quartz tube 23, which is filled with xenon in the ring space between the walls. Electrodes 24, 25 arranged on the inner and outer wall of the quartz tube 23 are connected to the operating device 21. The reaction chamber 19 is formed by an aluminum tube 26 with an internal mirror coating in which the xenon excimer emitter 22 is arranged and through which the exhaust gas 1 flows. The xenon excimer emitter 22 generates UV radiation with a main wavelength of 172 nm via which ozone is generated from the residual oxygen in the exhaust gas 1 and the nitrogen monoxide contained in the exhaust gas 1 is converted by this ozone into nitrogen dioxide. In the case of a comparatively low nitrogen monoxide concentration in the exhaust gas 1 (for example <5 ppm), it can be advantageous to throttle the intensity of the emitted UV radiation from the outset, which, in the exemplary embodiment depicted, occurs due to the fact that the outer electrode 24 is formed by a wire wound on the quartz tube 23.

As an alternative to the exemplary embodiment depicted, instead of a xenon excimer emitter 22, the ultraviolet light source 18 can also comprise two or more such emitters in one or more parallel tubes or it is possible to use at least one through-flow excimer lamp, such as that disclosed in the aforementioned EP 0 697 374 A1. It is also possible to use other types of lamps such as mercury (Hg) low-pressure vapor lamps operated with an electronic ballast or electrodelessly with radio-frequency excitation (energy input with microwave generator). However, especially in the case of a dielectrically impeded discharge based on xenon excimers, there is the advantage of immediate operational readiness compared to other discharge lamps wherein the illuminating gas only has to reach operating pressure after the ignition of the lamp. A further advantage compared to mercury vapor lamps is temperature independence.

Figure 3:
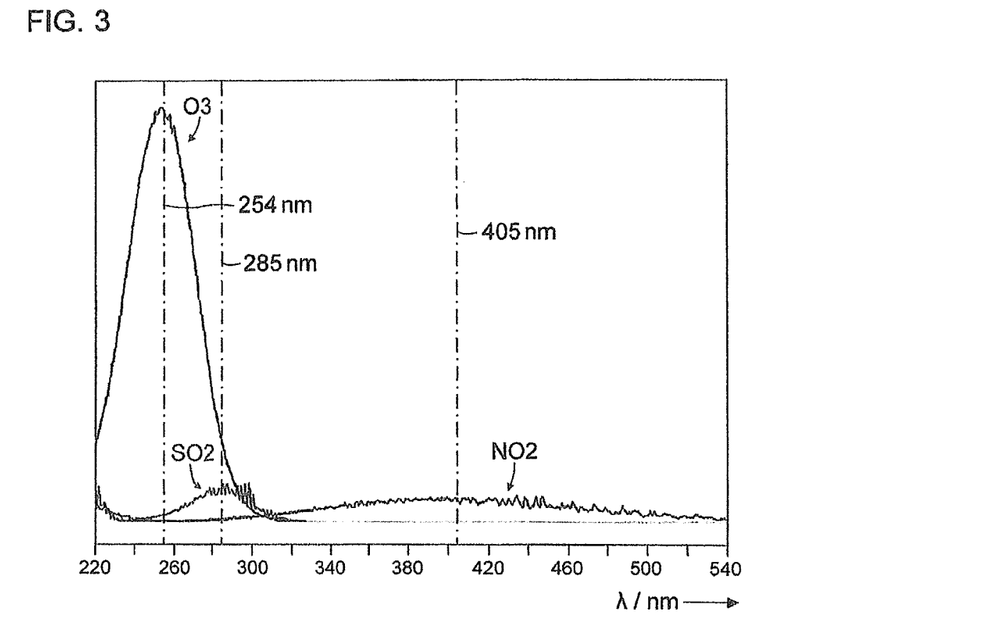
FIG. 3 is an exemplary graphical plot of the absorption spectra of nitrogen dioxide, ozone and sulfur dioxide and the emission spectra of the light-emitting diodes of the gas analyzer in accordance with the invention.

FIG. 3 shows, by way of example, a graphical plot of the absorption spectra of nitrogen dioxide NO2, ozone O3 and sulfur dioxide SO2 and the emission spectra of the two light-emitting diodes 2, 4, represented here by the central wavelengths 405 nm and 254 nm, for measuring the components nitrogen dioxide and ozone.

Returning to FIG. 1, the detector 12 that detects the light 3, 5 from the light-emitting diodes 2, 4 after it has passed through the measuring chamber 11 with the treated exhaust gas 1 generates a detector signal 27, which, according to the alternating actuation of the light-emitting diodes 2, 4, contains two alternately successive signal components of which a first signal component results from the light 3 from the first light-emitting diode 2 and a second signal component from the light from the second light-emitting diode 4. The reference detector 13 generates a reference signal 28 with reference-signal components that result from the light 3, 5 from the two light-emitting diodes 2, 4 and succeed each other in alternation. The detector signal 27 and the reference signal 28 are supplied to an evaluation device 29 containing a demultiplexer 30 for separating the different signal components. The multiplexer 7 and demultiplexer 30 are synchronized via a communication line 31 between the control device 6 and the evaluation device 29. After conditioning the signals 27, 28, for example, filtering and digitizing, a computing device 32 ascertains the nitrogen dioxide concentration from the first signal component of the detector signal 27 and the excess ozone concentration in the treated exhaust gas 1 in the measuring chamber 11 from the second signal component of the detector signal 27. Herein, the two signal components of the detector signal 27 are referenced with the associated signal components of the reference signal 28 so that the ascertained concentrations are independent of the brightness of the light-emitting diodes 2, 4 and hence, for example, of their state of ageing.

The ascertained nitrogen dioxide concentration in the treated exhaust gas 1 is output as the nitrogen oxide concentration 33 of the exhaust gas 1. The excess ozone concentration 34 ascertained is supplied as an actual value to a regulating device 35, which controls the ozone generator 18, here the operating device 21 of the UV emitter, in order to regulate the excess ozone concentration in the treated exhaust gas 1 to a prespecified setpoint value 36 in the form of a minimum residual ozone content. This ensures that only the amount of ozone required for the conversion of nitrogen monoxide into nitrogen dioxide is produced and, hence, the conversion of nitrogen monoxide into nitrogen dioxide is almost complete.

If the residual oxygen content of the exhaust gas 1 or the performance of the ozone generator 18 is not sufficient for the ozone generation required for the complete conversion of nitrogen monoxide into nitrogen dioxide, atmospheric oxygen 20 can be mixed with the exhaust gas 1 via the three-way mixing valve 16. The mixing can be performed manually or automatically depending on the ozone concentration 34 ascertained in the treated exhaust gas 1, for example, if the ozone concentration 34 falls below the setpoint value 36 by a prespecified amount.

Despite the aforementioned referencing of the measurements, thermostatic regulation of the entire photometric measuring arrangement of the gas analyzer is advantageous. This also includes thermostatic regulation of light-emitting diodes 2, 3 via Peltier elements 37, 38 in order to be able to achieve measuring ranges in the lower ppm range.

The illustrated gas analyzer can readily be expanded for the measurement of further constituents of the exhaust gas 1, such as carbon dioxide, carbon monoxide, sulfur compounds, chlorine and iodine compounds. Instead of the further suitable light sources required to this end (for example, light-emitting diodes), it is possible for individual existing light-emitting diodes to be provided with a luminescent material (phosphorus) that partially converts the light generated by the relevant light-emitting diode into light with a larger wavelength. This principle is, for example, disclosed in US 2010/049017 A1.

Figure 4:
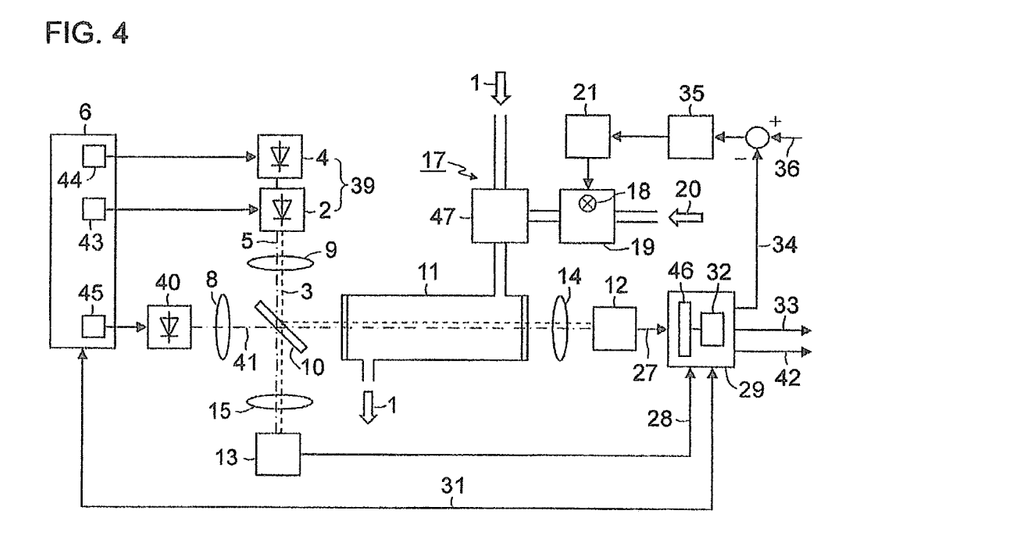
FIG. 4 is a second exemplary embodiment of the gas analyzer in accordance with the invention for measuring nitrogen oxides and sulfur dioxide.

FIG. 4 shows a second exemplary embodiment of the gas analyzer in accordance with the invention that differs from that shown in FIG. 1 in that the two light-emitting diodes 2, 4 (and possibly further light-emitting diodes, not shown here) are arranged adjacent to one another in an array 39. Here, the light-emitting diodes 2, 4 are depicted as arranged one behind the other purely for reasons of clarity of depiction. Here, instead of two collimator lenses for the two light-emitting diodes 2, 4, only the common collimator lens 9 is required.

Furthermore, a third light-emitting diode 40, which generates light 41 in the wavelength range of between 250 nm and 300 nm, for example, with a central wavelength of 285 nm, is provided for the measurement of the sulfur dioxide concentration in the exhaust gas 1.

FIG. 3 shows an exemplary graphical plot of the emission spectrum of the third light-emitting diode 40 represented by the central wavelength 285 nm.

The light 41 from the third light-emitting diode 40 is shaped via the collimator lens 8 into a parallel light bundle and guided by the beam splitter 10 together with the light 3, 5 from the first and second light-emitting diode 2, 4 in a partial beam through the measuring chamber 11 to the detector 12 and in a further partial beam to the reference detector 13. Therefore, the detector signal 27 receives a third signal component resulting from the light 41 from the third light-emitting diode 40 from which the evaluation device 29 ascertains the sulfur dioxide concentration 42 in the exhaust gas 1 in the measuring chamber 11.

A further difference consists in the fact that the light-emitting diodes 2, 4, 40 are not actuated in multiplex mode, but are modulated differently by signal generators 43, 44, 45, for example, with different modulation frequencies, clock-pulse rates or pulse codes. Accordingly, instead of a demultiplexer, the evaluation device 29 contains a demodulator 46 that is configured to demodulate or decode the signal components of the detector signal 27 and the reference signal 28 at the different modulation frequencies or clock-pulse rates in a phase-sensitive manner to separate the signal components for further processing and evaluation. The different arrangement of the light-emitting diodes 2, 4, 40 and their different actuation represent mutually independent measures which, accordingly, can be applied individually or together.

The ozone is now exclusively generated from atmospheric oxygen 20 and then mixed with the exhaust gas 1 to be treated in a mixing chamber 47. It should be understood the ozone can also be generated from the residual oxygen content of the exhaust gas 1 as shown in FIG. 1.

As shown in FIG. 3, there is a cross-sensitivity between the residual concentration of the ozone in the treated exhaust gas 1 and the measurement of the sulfur dioxide concentration, where it is readily possible to correct the sulfur dioxide concentration value with the value of the measured residual ozone concentration in a computational manner, however. Alternatively, as the following examples illustrate, the sulfur dioxide concentration can be measured in the untreated exhaust gas.

Figure 5:
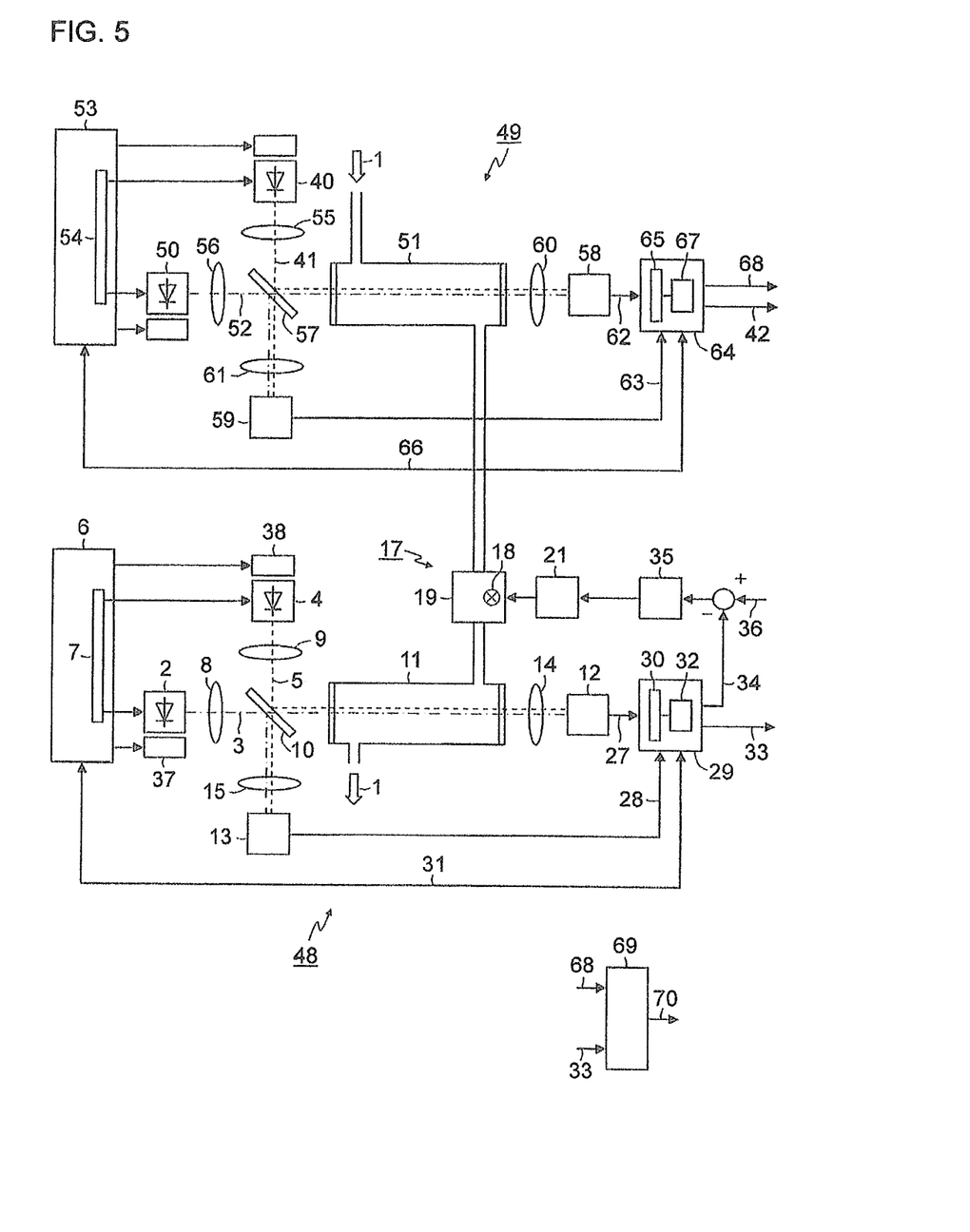
FIG. 5 is a third exemplary embodiment of the gas analyzer in accordance with the invention for measuring nitrogen oxides and sulfur dioxide.

FIG. 5 shows a third exemplary embodiment of the gas analyzer in accordance with the invention that is also used to measure the nitrogen oxide concentration, sulfur dioxide concentration and ozone concentration in the exhaust gas 1. Here, two analyzer units 48 and 49 of virtually identical design are used of which the analyzer unit 48 corresponds to the gas analyzer shown in FIG. 1 with the first and second light-emitting diode 2, 3, the measuring chamber 11 and the oxidation device 17 for measuring the nitrogen oxide concentration and ozone concentration in the treated exhaust gas 1.

The second analyzer unit 49 comprises a third light-emitting diode 40, a fourth light-emitting diode 50 and a further measuring chamber 51 through which the untreated exhaust gas 1 flows. In the illustrated example, the exhaust gas 1 flows successively through the further measuring chamber 51 of the analyzer unit 49, the oxidation device 17 and the measuring chamber 11 of analyzer unit 48. Alternatively, the exhaust gas 1 can be divided into a partial flow through the oxidation device 17 and the measuring chamber 11 of the analyzer unit 48 and a further partial flow parallel thereto through the further measuring chamber 51 of the analyzer unit 49.

The third light-emitting diode 40 generates light 41 in the wavelength range of between 250 nm and 300 nm, for example, with a central wavelength of 285 nm. The fourth light-emitting diode 50 generates light 52 in the same wavelength range as the first light-emitting diode 2, i.e., between 350 nm and 500 nm, for example, with a central wavelength of 405 nm.

The third and fourth light-emitting diode 40, 50 are actuated by a control device 53 which, in the exemplary embodiment depicted here, contains a multiplexer 54 in order to switch the light-emitting diodes 40, 50 on and off alternately. The light 41, 52 emitted by the light-emitting diodes 40, 50 is shaped via collimator lenses 55, 56 into parallel light bundles and divided a "polka dot" beam splitter 57 into a partial beam through the further measuring chamber 51 to a (further) detector 58 and a further partial beam to a (further) reference detector 59. The respective partial beams are focused on the detectors 58, 59 via lenses 60, 61.

The further detector 58 generates a further detector signal 62 with a third signal component resulting from the light 41 from the third light-emitting diode 40 and a fourth signal component resulting from the light 52 from the fourth light-emitting diode 50. The further reference detector 59 generates a further reference signal 63 with third and fourth reference-signal components resulting from the light 40, 52 from the third and fourth light-emitting diode 40, 51.

The further detector signal 62 and the reference signal 63 are fed to a further evaluation device 64, which contains a demultiplexer 65 for separating the different signal components. The synchronization of the multiplexer 54 and demultiplexer 65 occurs via a communication line 66 between the control device 53 and the evaluation device 64. The nitrogen dioxide concentration 68 in the untreated exhaust gas 1 in the measuring chamber 5 is ascertained from the third signal component of the detector signal 62 and the sulfur dioxide concentration 42 from the fourth signal component of the detector signal 62 in a computing device 67. Herein, the two signal components of the detector signal 62 are referenced with the associated signal components of the reference signal 63.

Therefore, the first analyzer unit 48 ascertains the nitrogen dioxide concentration of the UV-treated exhaust gas which, in the case of the almost complete conversion of nitrogen monoxide to nitrogen dioxide, corresponds to the nitrogen oxide concentration 33. In addition to the sulfur dioxide concentration 42, the second analyzer unit 49 ascertains the nitrogen dioxide concentration 68 in the untreated exhaust gas 1, so that the nitrogen monoxide concentration 70 in the exhaust gas 1 can be ascertained in a device 69 from the formation of the difference between the nitrogen dioxide concentrations 33, 68 ascertained by the two evaluation devices 29, 64 and output.

Figure 6:
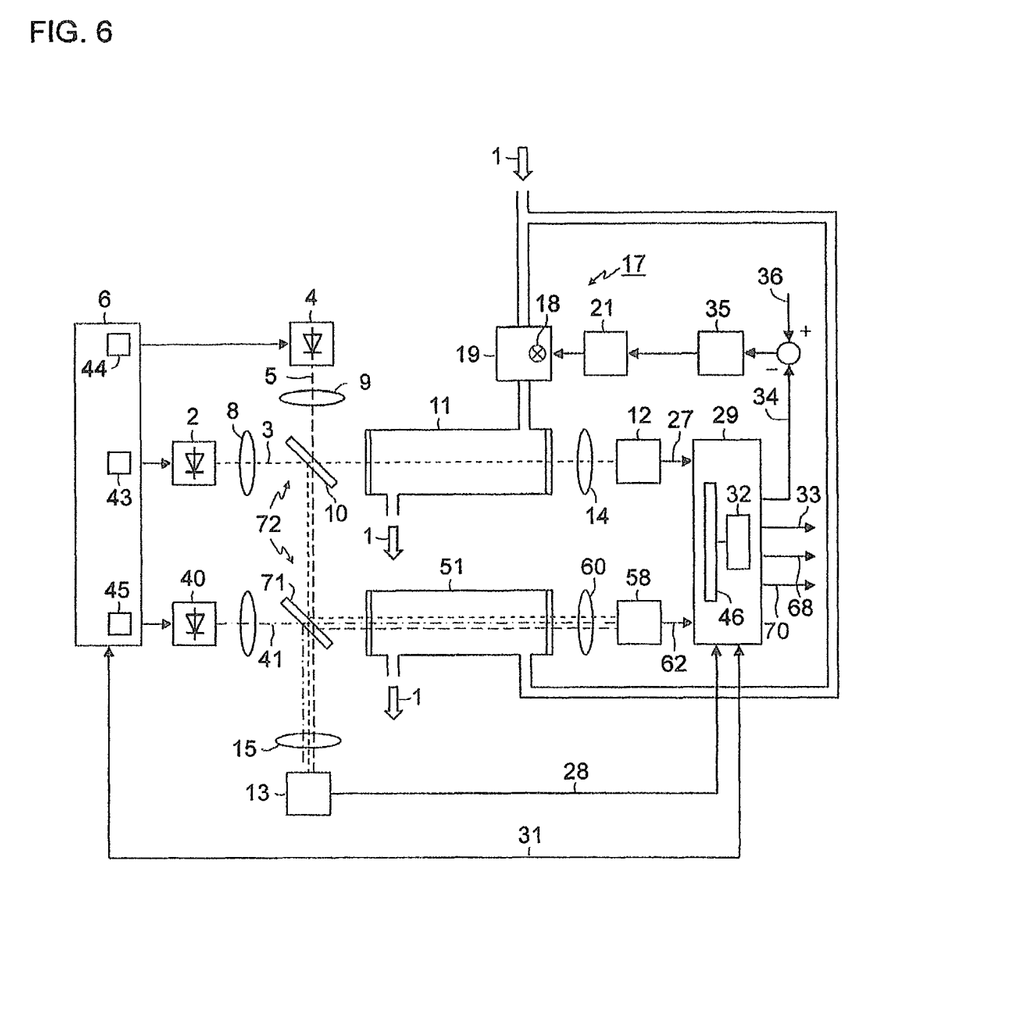
FIG. 6 a fourth exemplary embodiment of the gas analyzer in accordance with the invention for measuring nitrogen oxides and sulfur dioxide.

FIG. 6 shows a fourth exemplary embodiment of the gas analyzer in accordance with the invention in which the first, second and third light-emitting diodes 2, 4, 40, the measuring chamber 11, through which the UV-treated exhaust gas 1 flows, and the further measuring chamber 51, through which the untreated exhaust gas 1 flows, are structurally combined in an analyzer unit. The example shown represents an extension of the exemplary embodiment depicted in FIG. 4 by the further measuring chamber 51. Herein, a beam-splitter arrangement 72, here comprising the beam splitter 10 and a further beam splitter 71, diverts a first part of the light 3 from the first light-emitting diode 2 through the measuring chamber 11 through which the treated exhaust gas 1 flows to the detector 12 and a second part through the further measuring chamber 51 through which the untreated exhaust gas 1 flows to the further detector 58. A part of the light 5 from the second light-emitting diode 4 passes through the measuring chamber 11 through which the treated exhaust gas 1 flows to the detector 12 and a part of the light 41 from the third light-emitting diode 40 through the further measuring chamber 51 through which the untreated exhaust gas 1 flows to the further detector 58. A residual part of the light 3, 5, 41 from all the light-emitting diodes 2, 4, 40 is in each case guided to the reference detector 13.

As in the example in FIG. 4, the light-emitting diodes 2, 4, 40 are modulated differently by the signal generators 43, 44, 45 of the control device 6. In addition to the detector signal 29 of the detector 12, the evaluation device is also configured to process the further detector signal 62 of the further detector 58 and contains a demodulator 46, which demodulates the signal components of the detector signals 27, 62 and the reference signal 28 and separates them for further processing and evaluation in the computing device 32. The computing device 32 ascertains the nitrogen dioxide concentration in the treated exhaust gas 1, and hence the nitrogen oxide concentration 33, from the first signal component of the detector signal 27 resulting from the light 3 from the first light-emitting diode 2. The ozone concentration 34 in the treated exhaust gas 1 is determined from the second signal component of the detector signal 27 resulting from the light 5 from the second light-emitting diode 2. The sulfur dioxide concentration 42 in the exhaust gas 1 is ascertained from the third signal component in the further detector signal 62 resulting from the light 41 from the third light-emitting diode 40. The nitrogen dioxide concentration 68 in the untreated exhaust gas 1 is ascertained from the fourth signal component of the detector signal 27 in the further detector signal 62 resulting from the light 3 from the first light-emitting diode 2. Finally, the nitrogen monoxide concentration 70 in the exhaust gas 1 is ascertained from the difference between the nitrogen dioxide concentrations 33, 68 measured in the treated and the untreated exhaust gas 1.

Figure 7:
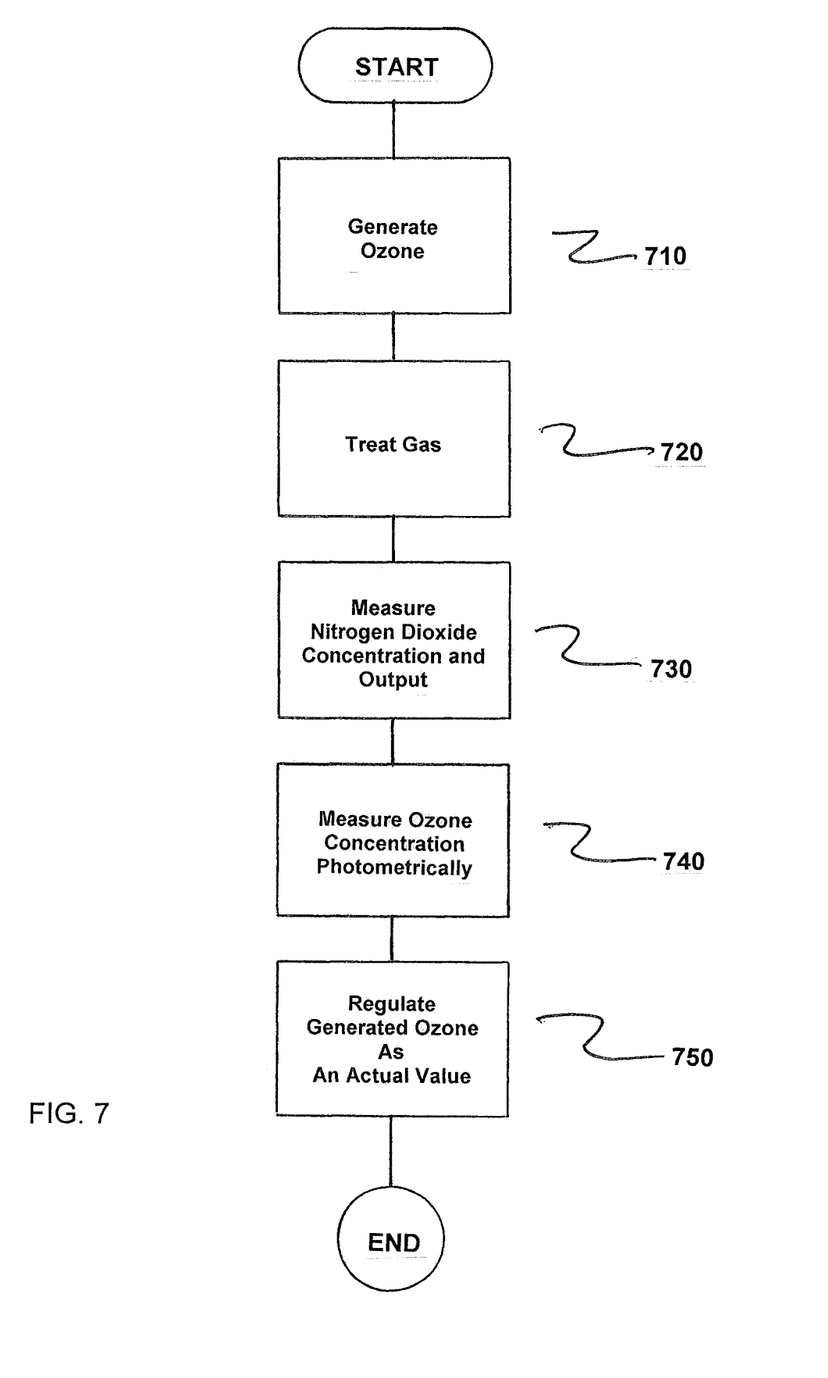
FIG. 7 is a flowchart of the method in accordance with the invention.

FIG. 7 is a flowchart of the method for measuring nitrogen oxides in an exhaust gas 1. The method comprises generating ozone is generated from oxygen, as indicated in step 710.

Next, the exhaust gas 1 is treated with the generated ozone to convert nitrogen monoxide within the exhaust gas 1 into nitrogen dioxide, as indicated in step 720.

The nitrogen dioxide concentration in the treated exhaust gas 1 is measured photometrically via a first light-emitting diode 2 which emits with a central wavelength of between 350 nm and 500 nm and the measured concentration is output as the nitrogen oxide concentration 33 in the exhaust gas 1, as indicated in step 730.

Next, the ozone concentration in the treated exhaust gas 1 is measured photometrically via a second light-emitting diode 4 which emits with a central wavelength of between 250 nm and 265 nm, as indicated in step 740.

The generation of the ozone via the measured ozone concentration is now regulated as an actual value 34 to a pre-specified setpoint value 36, as indicated in step 750.

Thus, while there have been shown, described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A gas analyzer for measuring nitrogen oxides in an exhaust gas comprising:
    an oxidation device comprising an ozone generator for generating ozone from oxygen and configured to treat the exhaust gas with the ozone to convert nitrogen monoxide within the exhaust gas into nitrogen dioxide;
    a first light-emitting diode which emits with a central wavelength of between 350 nm and 500 nm;
    a second light-emitting diode which emits with a central wavelength of between 250 nm and 265 nm;
    a measuring chamber through which the treated exhaust gas flows and light from the first light-emitting diode and light from the second light-emitting diode pass;
    a detector which detects the light from the first light-emitting diode and the light from the second light-emitting diode after said light passes through the measuring chamber and which generates a detector signal with a first signal component resulting from the light from the first light-emitting diode and a second signal component resulting from the light from the second light-emitting diode;
    an evaluation device which ascertains nitrogen dioxide concentration in the treated exhaust gas in the measuring chamber from the first signal component and outputs said concentration as the nitrogen oxide concentration in the exhaust gas and ascertains ozone concentration in the exhaust gas in the measuring chamber from the second signal component; and
    a regulating device which controls the ozone generator and obtains the ascertained ozone concentration as an actual value to regulate said concentration to a pre-specified setpoint value.

2. The gas analyzer as claimed in claim 1, further comprising:
    a beam splitter which diverts a part of the lights from the first and second light-emitting diodes to a reference detector;
    wherein that the reference detector generates a reference signal with first and second reference-signal components resulting from the light from the first and second light-emitting diode; and wherein the evaluation device references the signal components of the detector signal with the associated reference-signal components.

3. The gas analyzer as claimed in claim 2, wherein the ozone generator comprises an ultraviolet light source.

4. The gas analyzer as claimed in claim 1, wherein the ozone generator comprises an ultraviolet light source.

5. The gas analyzer as claimed in claim 4, wherein the ultraviolet light source comprises at least one xenon excimer emitter.

6. The gas analyzer as claimed in claim 5, wherein the ultraviolet light source is arranged in a closed reaction chamber through which the exhaust gas flows and which is configured to generate the ozone from a residual oxygen content of the exhaust gas.

7. The gas analyzer as claimed in claim 4, wherein the ultraviolet light source is arranged in a closed reaction chamber through which the exhaust gas flows and which is configured to generate the ozone from a residual oxygen content of the exhaust gas.

8. The gas analyzer as claimed in claim 1, further comprising:
a third light-emitting diode which emits with a central wavelength of between 250 nm and 300 nm, light emitted by the third light-emitting diode also passing through the measuring chamber and subsequently being detected by the detector such that the detector signal contains a third signal component resulting from the light from the third light-emitting diode; and
wherein the evaluation device ascertains a sulfur dioxide concentration in the exhaust gas in the measuring chamber from the third signal component.

9. The gas analyzer as claimed in claim 8, further comprising:
a beam splitter which diverts a part of the lights from the first and second light-emitting diodes to a reference detector;
wherein that the reference detector generates a reference signal with first and second reference-signal components resulting from the light from the first and second light-emitting diode;
wherein the evaluation device references the signal components of the detector signal with the associated reference-signal components; and
wherein the beam splitter diverts a part of the light from the third light-emitting diode to the reference detector such that the reference signal contains a third reference-signal component resulting from the light from the third light-emitting diode and such that the evaluation device references the third signal component of the detector signal with the third reference-signal component.

10. The gas analyzer as claimed in claim 1, further comprising:
a third light-emitting diode which emits with a central wavelength of between 250 nm and 300 nm;
a fourth light-emitting diode which emits with a central wavelength of between 350 nm and 500 nm with the same central wavelength as the first light-emitting diode;
a further measuring chamber through which the untreated exhaust gas flows and the light from the third and fourth light-emitting diode passes;
a further detector which detects the light from the third and fourth light-emitting diode after said light has passed through the further measuring chamber and which generates a further detector signal with a third signal component resulting from the light from the third light-emitting diode and a fourth signal component resulting from the light from the fourth light-emitting diode;
a further evaluation device which ascertains a sulfur dioxide concentration in the untreated exhaust gas in the further measuring chamber from the third signal component and nitrogen dioxide concentration from the fourth signal component; and
a device which outputs a difference between the nitrogen dioxide concentrations ascertained by the two evaluation devices as the nitrogen monoxide concentration in the exhaust gas.

11. The gas analyzer as claimed in claim 10, further comprising:
a further beam splitter which diverts a part of the light from the third and fourth light-emitting diode to a further reference detector,
wherein the further reference detector generates a further reference signal with third and fourth reference-signal components resulting from the light from the third and fourth light-emitting diode; and
wherein the further evaluation device references the third and fourth signal components of the further detector signal with associated reference-signal components.

12. The gas analyzer as claimed in claim 1, further comprising:
a third light-emitting diode which emits with a central wavelength of between 250 nm and 300 nm;
a further measuring chamber through which the untreated exhaust gas flows and the light from the third light-emitting diode passes;
a beam-splitter arrangement which conducts a part of the light from the first light-emitting diode through the further measuring chamber;
a further detector which detects the light from the first and third light-emitting diodes after said light has passed through the further measuring chamber and which generates a further detector signal with a third signal component resulting from the light from the third light-emitting diode and a fourth signal component resulting from the light from the first light-emitting diode;
wherein the evaluation device further ascertains a sulfur dioxide concentration in the untreated exhaust gas in the further measuring chamber from the third signal component and the nitrogen dioxide concentration from the fourth signal component and outputs a difference between the nitrogen dioxide concentrations ascertained from the first and fourth signal components as the nitrogen monoxide concentration in the exhaust gas.

13. The gas analyzer as claimed in claim 12, wherein the beam-splitter arrangement is configured to divert a part of the lights from the first, second and third light-emitting diodes to a reference detector which generates a reference signal with reference-signal components resulting from the light from the light-emitting diodes; and wherein the evaluation device references the signal components of the detector signals with the associated reference-signal components.

14. A method for measuring nitrogen oxides in an exhaust gas, the method comprising:
generating ozone is generated from oxygen;
treating the exhaust gas with the generated ozone to convert nitrogen monoxide within the exhaust gas into nitrogen dioxide;
measuring the nitrogen dioxide concentration in the treated exhaust gas photometrically via a first light-emitting diode which emits with a central wavelength of between 350 nm and 500 nm and outputting the measured concentration as the nitrogen oxide concentration in the exhaust gas;

measuring the ozone concentration in the treated exhaust gas photometrically via a second light-emitting diode which emits with a central wavelength of between 250 nm and 265 nm; and regulating the generation of the ozone via the measured ozone concentration as an actual value to a prespecified setpoint value.

15. The method as claimed in claim 14, wherein a sulfur dioxide concentration in the treated or untreated exhaust gas is measured photometrically via a third light-emitting diode which emits with a central wavelength of between 250 nm and 300 nm.

16. The method as claimed in claim 15, wherein the nitrogen dioxide concentration in the untreated exhaust gas is measured photometrically via a fourth light-emitting diode which emits with a central wavelength of between 350 nm and 500 nm with the same central wavelength as the first light-emitting diode and the nitrogen monoxide concentration in the exhaust gas is ascertained from a difference between the nitrogen dioxide concentrations ascertained in the treated exhaust gas and in the untreated exhaust gas.

17. The method as claimed in claim 14, wherein the nitrogen dioxide concentration in the untreated exhaust gas is measured photometrically via a fourth light-emitting diode which emits with a central wavelength of between 350 nm and 500 nm with the same central wavelength as the first light-emitting diode and the nitrogen monoxide concentration in the exhaust gas is ascertained from a difference between the nitrogen dioxide concentrations ascertained in the treated exhaust gas and in the untreated exhaust gas.

\* \* \* \* \*